United States Patent
Most et al.

(10) Patent No.: US 7,427,691 B2
(45) Date of Patent: Sep. 23, 2008

(54) RESOLUTION OF P-HYDROXYPHENYL-2-ALKOXYPROPIONIC ACIDS

(75) Inventors: Dieter Most, Bruchkoebel (DE); Kai Rossen, Hanau (DE); Michael Schwarm, Alzenau (DE)

(73) Assignee: Degussa GmbH, Duesseldorf (DE)

( * ) Notice: Subject to any disclaimer, the term of this patent is extended or adjusted under 35 U.S.C. 154(b) by 7 days.

(21) Appl. No.: 11/570,077

(22) PCT Filed: Jul. 6, 2005

(86) PCT No.: PCT/EP2005/007273

§ 371 (c)(1),
(2), (4) Date: Dec. 6, 2006

(87) PCT Pub. No.: WO2006/007976

PCT Pub. Date: Jan. 26, 2006

(65) Prior Publication Data

US 2008/0064897 A1 Mar. 13, 2008

(30) Foreign Application Priority Data

Jul. 20, 2004 (DE) .................. 10 2004 035 034

(51) Int. Cl.
*C07C 65/00* (2006.01)
*C07C 65/01* (2006.01)
*C07C 59/00* (2006.01)

(52) U.S. Cl. .................. 562/478; 562/465; 562/470

(58) Field of Classification Search .................. None
See application file for complete search history.

(56) References Cited

U.S. PATENT DOCUMENTS

| 3,234,268 A | 2/1966 | Merica et al. | |
|---|---|---|---|
| 6,559,335 B2 * | 5/2003 | Kumar et al. | 560/61 |
| 7,002,037 B2 * | 2/2006 | Andersson et al. | 560/27 |

FOREIGN PATENT DOCUMENTS

WO  01 40159  6/2001

OTHER PUBLICATIONS

Kolarvic et al., Tetrahedron Letters (2001), 42(13), 2579-2582.*

* cited by examiner

*Primary Examiner*—Karl J Puttlitz
(74) *Attorney, Agent, or Firm*—Oblon, Spivak, McClelland, Maier & Neustadt, P.C.

(57) ABSTRACT

The present invention is aimed at a process for the preparation of enantiomerically enriched compounds of general formula (I). These are obtained by classical resolution of the corresponding acid using a chiral amino base in organic solvents.

(I)

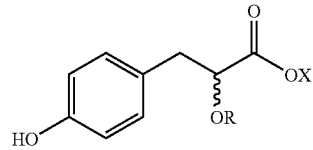

18 Claims, No Drawings

RESOLUTION OF P-HYDROXYPHENYL-2-ALKOXYPROPIONIC ACIDS

The present invention is aimed at a process for the preparation of enantiomerically enriched compounds of the general formula (I)

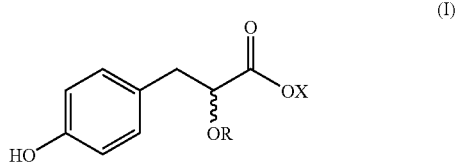

(I)

Compounds of the general formula (I) are important starting substances for the preparation of bioactive compounds. In particular, the enantiomerically enriched derivatives of the formula (I) are employed for the preparation of active compounds against "insulin resistance syndrome" (IRS).

In WO 0140159 and WO 0224625, processes for the preparation of enantiomerically enriched esters and other derivatives of the general formula (I) by resolution of the racemic precursor compounds are mentioned. WO 0140159 discloses in detail the separation of the corresponding racemic mixtures by the crystallization of diastereomeric pairs of salts, the crystallization or chromatography of diastereomeric compounds of the general formula (I) obtained by substitution, and the chromatography on chiral phases and the enantioselective hydrogenation of an unsaturated precursor of formula (I). The crystallization of the diastereomeric pairs of salts addressed here proceeds via chiral amines, of which, however, only (S)-(−)-1-(1-naphthyl)ethylamine is documented as an example in relation to the compound of the general formula (I) protected on the phenolic OH group.

WO 0224625 likewise mentions the resolution of compounds of the general formula (I) in the presence of chiral bases. As examples of chiral bases, (R)-(+)-α-methylbenzylamine, (S)-(+)-phenylglycinol, quinidine, ephedrine, N-octyl-glucaramine and N-methylglucaramine are explicitly mentioned. In turn, only the crystallization of a compound of the general formula (I) protected on the phenolic OH group is described.

It is the object of the present invention to indicate a further process for the preparation of enantiomerically enriched compounds of the general formula (I), which in particular is in the position also to prepare the compounds of the general formula (I) unprotected on the phenolic OH group needed for the preparation of the bioactive compounds by means of classical resolution other than via an additional protection and deprotection step.

These and further objects are achieved by a process for the preparation of enantiomerically enriched compounds of the general formula (I)

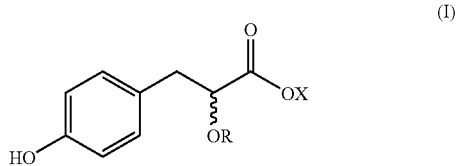

(I)

in which

X=H, alkali metal ion, alkaline earth metal ion,

R represents a ($C_1$-$C_8$)-alkyl radical, which comprises crystallization of a compound of the general formula (I), in which X=H, with enantiomerically pure 2-amino-1-butanol with salt formation in an organic solvent or solvent mixture selected from the group consisting of alcohols, esters, ketones and ethers. By said process, the object set is achieved in a surprising and nonetheless advantageous manner. By the combination of the use of a specific chiral amine and a selected organic solvent or solvent mixture, it is possible to be able in the resolution to dispense with the protection and deprotection step of the phenolic OH group suggested by the prior art.

The reaction according to the invention can preferably be used with those derivatives of the general formula (I) where X=H, in which R is an alkyl radical having 1 to 4 C atoms. A process is very particularly preferred in which a compound of the formula (I) where X=H is employed, in which R=methyl or ethyl.

Within the scope of the organic solvent or solvent mixtures indicated above, the person skilled in the art is free to choose which he employs in the classical resolution. Preferred esters can be ethyl acetate, isopropyl acetate, butyl acetate, methyl acetate. Ethers preferably to be chosen are methyl tert-butyl ether, diisopropyl ether, diethyl ether, THF, diphenyl ether, dioxane. Possible alcohols are in particular those such as methanol, ethanol, propanol, isopropanol or sec- or n-butanol. Organic ketones can preferably be acetone, MIBK, diisopropylketone. Very particularly preferably, the organic solvent used in the resolution is a mixture of ketones and alcohols. Highly preferred is the use of a mixture of MIBK/isopropanol in the ratio 10:1 to 0.1:1, preferably 5:1 to 0.2:1, more preferably 4:1 to 0.3:1 and very particularly preferably in the range from 3:1 to 0.5:1 (v/v).

The molar ratio between racemic mixture of the general formula (I) employed where X=H and the enantiomerically pure chiral cleavage reagent preferably lies in a range from 0.3 to 1.2, preferably between 0.35 and 1.1 and very particularly preferably between 0.4 and 1.

The invention furthermore relates to the two diastereomeric pairs of salts of (S)-3-(4-hydroxyphenyl)-2-($C_1$-$C_8$)-alkyl-oxypropionic acid and (S)-(+)-2-amino-1-butanol, and of (R)-3-(4-hydroxyphenyl)-2-($C_1$-$C_8$)-alkyloxypropionic acid and (R)-(−)-2-amino-1-butanol and their use for the preparation of bioactive compounds.

In the present invention, a procedure is preferably used in which the racemic mixture of the formula (I) where X=H is dissolved in appropriate organic solvents or solvent mixtures, the solution is warmed to a temperature of greater than 30, preferably greater than 40, very particularly preferably greater than 50 degrees Celsius to at most 100 degrees Celsius and subsequently the chiral cleavage reagent is added. The temperature of the reaction mixture is then slowly cooled to room temperature. In this phase, seed crystals consisting of the salts according to the invention are added at not more than 30 degrees Celsius. Subsequently, the reaction mixture is stirred at room temperature and filtered off after completion of the crystallization. The filter cake is washed with an organic solvent and subsequently dried in vacuo. The salt according to the invention is obtained in very good yields of more than 40 percent and extremely good diastereoselectivities. The further workup, in particular the liberation of the compound of the formula (I) where X=H, takes place according to process variants known to the person skilled in the art (acidification and extraction or by means of ion exchange. chromatography). If necessary, it is possible beforehand, however, also to carry out a further recrystallization of the diastereomeric pair of salts. In this way, the optical purity of the compound of the formula (I) can be increased to values of >99% ee. If desired, subsequently the enantiomerically pure compound of the formula (I) where X=H can be converted by esterification or salt formation to the corresponding derivatives of the formula (I) where X=alkali metal ion, alkaline earth metal ion or R.

($C_1$-$C_8$)-Alkyl is to be regarded as all alkyl radicals having a number of C atoms from one to eight, for example methyl, ethyl, n-propyl, isopropyl, n-butyl, isobutyl, sec-butyl, tert-butyl, pentyl, hexyl, heptyl or octyl together with all bonding isomers.

EXAMPLES

Preparation of the (S,S)-ammonium Salt 78.4 g (0.4 mol) of racemic (R,S)-3-(4-hydroxyphenyl)-2-methoxypropionic acid are dissolved in 400 ml of methyl isobutyl ketone and 160 ml of isopropanol. The solution is warmed to 50° C. and at this temperature 36.4 g (0.4 mol) of (S)-(+)-2-amino-1-butanol are added dropwise in the course of 15 minutes. The reaction mixture is slowly cooled to room temperature. At 30° C., seed crystals are added. The reaction mixture is stirred for 12 h at RT. The precipitated (S,S)-ammonium salt is filtered off at RT. The filter cake is washed with 20 ml of acetone and subsequently dried in vacuo at 400C. 45.9 g (40%) of (S,S)-ammonium salt of (S)-3-(4-hydroxyphenyl)-2-methoxypropionic acid and (S)-(+)-2-amino-1-butanol are obtained.

Cleavage of the (S,S)-ammonium Salt 45.9 g of (S,S)-ammonium salt are dissolved in 250 ml of DI-water. With stirring, about 16 ml of concentrated hydrochloric acid (36% strength) are added dropwise such that a pH of pH=0.8-1 is established. The aqueous phase is extracted three times with 275 ml each of MIBK. The combined extracts are completely concentrated in vacuo at 50° C. The resulting oil slowly crystallizes completely. 33.0 g of crude (S)-3-(4-hydroxyphenyl)-2-methoxypropionic acid having an optical purity of ee=92.0% are obtained. The oil can also be made to crystallize in a controlled manner. To this end, the oil is dissolved in 75 ml of methyl tert-butyl ether at 40-50° C. and then 125 ml of cyclohexane are slowly added dropwise with stirring. The solution is slowly cooled to room temperature. At 30° C., seed crystals are added. After 4 h at RT, the product is filtered off and the filter cake is washed with 10 ml of the methyl tert-butyl ether/cyclohexane mixture. After drying in vacuo at 50° C., 30.0 g (38%) of (S)-3-(4-hydroxyphenyl)-2-methoxypropionic acid are obtained. Optical purity ee>99%. Chemical purity>99%

45.9 g of (S,S)-ammonium salt are dissolved in 250 ml of DI-water. With stirring, about 16 ml of concentrated hydrochloric acid (36% strength) are added dropwise such that a pH of pH=0.8-1 is established. The aqueous phase is extracted three times with 275 ml each of MIBK. The combined extracts are concentrated down to a residual volume of 420 ml in vacuo.

Neutralization of the (S)-3-(4-hydroxyphenyl)-2-methoxy-propionic Acid Using Sodium Acetate 420 ml of the (S)-3-(4-hydroxyphenyl)-2-methoxypropionic acid solution from above are treated with stirring with a solution of 16.32 g of sodium acetate in 136 ml of methanol. After addition of seed crystals, the mixture is stirred for 12 h at room temperature. The precipitated product is filtered off and the filter cake is washed twice with 20 ml each of MIBK. The product is dried in vacuo at 50° C. in the course of 12 h. 30.2 g (34.8%) of sodium (S)-3-(4-hydroxyphenyl)-2-methoxypropionate are obtained. Optical purity ee=95-97%. Chemical purity >99%.

Improvement of the Optical Purity 10 g of sodium (S)-3-(4-hydroxyphenyl)-2-methoxypropionate having an optical purity of ee=95% are resuspended with stirring in 40 ml of methanol at 40° C. After cooling to RT, the product is isolated by filtration. The filter cake is washed with 5 ml of cold methanol and subsequently dried in vacuo at 50° C. in the course of 12 h. 9 g of sodium (S)-3-(4-hydroxyphenyl)-2-methoxypropionate having an optical purity of ee=99.6% are obtained.

Preparation of the (R,R)-ammonium Salt 19.9 g (0.1015 mol) of (R)-3-(4-hydroxyphenyl)-2-methoxy-propionic acid are dissolved in 150 ml of MTBE. At RT, 9.05 g (0.1015 mol) of (R)-(−)-2-amino-1-butanol are slowly added dropwise with stirring. The reaction mixture is stirred for 4 h at RT. The precipitate is filtered off and the filter cake is washed with 10 ml of MTBE. After drying, 26 g (90%) of crystalline (R,R)-ammonium salt are obtained.

The following experiments demonstrate that both the (R,S)-ammonium salt and the (S,R)-ammonium salt were obtained in the form of oils which show no tendency at all to crystallize.

Preparation of the (R,S)-ammonium Salt 19.9 g (0.1015 mol) of (R)-(−)-3-(4-hydroxyphenyl)-2-methoxypropionic acid are dissolved in 150 ml of MTBE. At RT, 9.05 g (0.1015 mol) of (S)-(+)-2-amino-1-butanol are added dropwise with stirring, the product separating as an oil. The mixture was stirred for 12 h at RT. A two-phase mixture resulted. After phase separation, the lower phase was separated off and freed of volatile constituents in vacuo. 31.8 g of spectroscopically homogeneous product result in the form of an oil which shows no tendency at all to crystallize. The experiments were repeated in various solvents. In all cases, it was not possible to achieve any crystallization.

Preparation of the (S,R)-ammonium Salt 13.72 g (0.07 mol) of (S)-3-(4-hydroxyphenyl)-2-methoxypropionic acid are dissolved in 100 ml of MTBE and 6.2 g (0.07 mol) of (R)-(−)-2-amino-1-butanol are added dropwise at RT with stirring, the product separating as an oil. The mixture was stirred for 12 h at RT. A two-phase mixture resulted.

After phase separation, the lower phase was separated off and freed in vacuo of volatile constituents. 22.3 g of spectroscopically homogeneous product resulted in the form of an oil which showed no tendency at all to crystallize.

The experiments were repeated in various solvents. In all cases, it was not possible to achieve any crystallization.

The invention claimed is:

1. Process for the preparation of enantiomerically enriched compounds of the general formula (I)

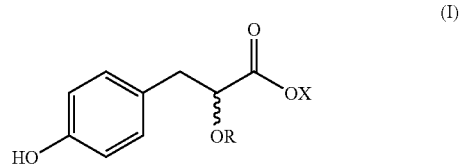

(I)

comprising:
crystallizing a compound of the general formula (I) in which X=H with enantiomerically pure 2-amino-1-butanol with salt formation in an organic solvent or solvent mixture selected from the group consisting of alcohols, esters, ketones and ethers, wherein X is selected from the group consisting of H, alkali metal ion, alkaline earth metal ion, and R represents a $(C_1-C_8)$-alkyl radical.

2. Process according to claim 1, wherein R=methyl or ethyl.

3. Process according to claim 1, wherein the organic solvent used is a mixture of ketones and alcohols.

4. Process according to claim 1, wherein the molar ratio between (I) where X=H and 2-amino-1-butanol is in the ratio 1 to 0.4-1.

5. A salt of (S)-3-(4-hydroxyphenyl)-2-$(C_1-C_8)$-alkyloxypropionic acid and (S)-(+)-2-amino-1-butanol.

6. A salt of (R)-3-(4-hydroxyphenyl)-2-$(C_1-C_8)$-alkyloxypropionic acid and (R)-(−)-2-amino-1-butanol.

7. A method for the preparation of bioactive compounds which comprises reacting the salt of claim 5 as a starting substance.

8. Process for the preparation of enantiomerically enriched compounds of the general formula (I)

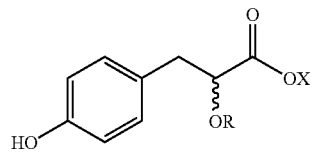

(I)

comprising forming a salt of the compound of general formula (I) in which X=H with enantiomerically pure 2-amino-1-butanol in an organic solvent or solvent mixture selected from the group consisting of alcohols, esters, ketones and ethers; and crystallizing the salt from the organic solvent or solvent mixture; wherein, X is at least one selected from the group consisting of H, alkali metal ion alkaline earth metal ion and wherein R represents a $C_1-C_8$ alkyl radical.

9. A method for the preparation of bioactive compounds which comprises reacting the salt of claim 6 as a starting substance.

10. Process according to claim 3, wherein the mixture is of methylisobutylketone and isopropanol.

11. Process according to claim 10, wherein the ratio of methylisobutylketone and isopropanol is from 10:1 to 0.1:1 (v/v).

12. Process according to claim 10, wherein the ratio of methylisobutylketone and isopropanol is from 5:1 to 0.2:1 (v/v).

13. Process according to claim 10, wherein the ratio of methylisobutylketone and isopropanol is from 4:1 to 0.3:1 (v/v).

14. Process according to claim 10, wherein the ratio of methylisobutylketone and isopropanol is from 3:1 to 0.5:1 (v/v).

15. An (S,S) ammonium salt of (S)-3-(4-hydroxyphenyl)-2-methoxypropionic acid and (S)-(+)-2-amino-1-butanol.

16. An (R,R) ammonium salt of (R)-3-(4-hydroxyphenyl)-2-methoxypropionic acid and (R)-(+)-2-amino-1-butanol.

17. An (R,S) ammonium salt of (R)-3-(4-hydroxyphenyl)-2-methoxypropionic acid and (S)-(+)-2-amino-1-butanol.

18. An (S,R) ammonium salt of (S)-3-(4-hydroxyphenyl)-2-methoxypropionic acid and (R)-(+)-2-amino-1-butanol.

* * * * *